(12) United States Patent
Winter

(10) Patent No.: US 10,792,036 B2
(45) Date of Patent: Oct. 6, 2020

(54) METHOD AND APPARATUS FOR DOUBLE LOOP STITCHING

(71) Applicant: Lia Lynn Winter, Knoxville, TN (US)

(72) Inventor: Lia Lynn Winter, Knoxville, TN (US)

(73) Assignee: Winter Innovations, LLC, Knoxville, TN (US)

( * ) Notice: Subject to any disclaimer, the term of this patent is extended or adjusted under 35 U.S.C. 154(b) by 210 days.

(21) Appl. No.: 16/151,591

(22) Filed: Oct. 4, 2018

(65) Prior Publication Data

US 2019/0142417 A1    May 16, 2019

Related U.S. Application Data

(60) Provisional application No. 62/586,690, filed on Nov. 15, 2017.

(51) Int. Cl.
  *A61B 17/06* (2006.01)
  *A61B 17/04* (2006.01)
  (Continued)

(52) U.S. Cl.
  CPC .... *A61B 17/06066* (2013.01); *A61B 17/0485* (2013.01); *A61B 2017/06052* (2013.01);
  (Continued)

(58) Field of Classification Search
  CPC ........ A61B 17/06066; A61B 2017/061; A61B 2017/06052
  See application file for complete search history.

(56) References Cited

U.S. PATENT DOCUMENTS

| | | |
|---|---|---|
| 1,293,660 A | 2/1919 | Armstrong |
| 1,591,021 A | 7/1926 | Davis |
| (Continued) | | |

FOREIGN PATENT DOCUMENTS

| | | |
|---|---|---|
| CA | 1312518 | 1/1993 |
| CN | 102164548 A | 8/2011 |
| (Continued) | | |

OTHER PUBLICATIONS

International Search Report and Written Opinion of counterpart PCT Application No. PCT/US2019/021772 filed Mar. 12, 2019.

*Primary Examiner* — Melanie R Tyson
(74) *Attorney, Agent, or Firm* — Chambliss, Bahner & Stophel, P.C.; Stephen D. Adams

(57) ABSTRACT

A sewing needle having a needle tip configured to pass through a sewing material and a first needle portion that follows the needle tip. A second needle portion is removably connected to the first needle portion and includes an end that is inserted into an elongate hollow receiver located on the first needle portion. The second needle portion follows the needle tip through said sewing material substantially simultaneously with the first needle portion. A first thread connection formed on the first needle portion is configured to carry a first portion of said thread through the sewing material and a second thread connection formed on the second needle portion is configured to carry a second portion of said thread through the sewing material. After passing through the sewing material, the first and second needle portions are separated, brought around outside edges of the sewing material and reconnected for subsequent stitching.

18 Claims, 11 Drawing Sheets

(51) Int. Cl.
*D05B 97/00* (2006.01)
*A61F 2/08* (2006.01)

(52) U.S. Cl.
CPC .............. *A61F 2/08* (2013.01); *A61F 2/0811* (2013.01); *A61F 2002/0882* (2013.01); *A61F 2220/0075* (2013.01); *A61F 2240/001* (2013.01); *D05B 97/00* (2013.01)

(56) References Cited

U.S. PATENT DOCUMENTS

| | | | |
|---|---|---|---|
| 5,368,595 | A | 11/1994 | Lewis |
| 7,326,247 | B2 | 2/2008 | Schmieding et al. |
| 7,846,170 | B2 | 12/2010 | Modesitt et al. |
| 8,298,284 | B2 | 10/2012 | Cassani |
| 8,388,653 | B2 | 3/2013 | Nobis et al. |
| 8,591,544 | B2 | 11/2013 | Jolly et al. |
| 9,480,565 | B2 | 11/2016 | Medema et al. |
| 9,545,251 | B2 | 1/2017 | Bojarski et al. |
| 9,622,742 | B2 | 4/2017 | Spenciner |
| 9,993,241 | B2 | 6/2018 | Denham et al. |
| 9,993,332 | B2 | 6/2018 | Woodruff et al. |
| 2002/0058959 | A1* | 5/2002 | Gellman ............... A61F 2/0036 606/185 |
| 2007/0060788 | A1 | 3/2007 | Gellman |
| 2007/0173887 | A1 | 7/2007 | Sasaki |
| 2008/0051833 | A1* | 2/2008 | Gramuglia ....... A61B 17/06128 606/222 |
| 2009/0105752 | A1 | 4/2009 | Shonteff et al. |
| 2011/0213387 | A1 | 9/2011 | Nguyen et al. |
| 2011/0264138 | A1* | 10/2011 | Avelar .................. A61B 90/94 606/228 |
| 2012/0046746 | A1 | 2/2012 | Konicek |
| 2013/0289597 | A1 | 10/2013 | Guo |
| 2016/0175088 | A1 | 6/2016 | Sengun |
| 2016/0206307 | A1 | 7/2016 | Wack et al. |
| 2016/0338696 | A1* | 11/2016 | Loubens .......... A61B 17/06109 |
| 2017/0172725 | A1 | 6/2017 | Gustafson |
| 2017/0303956 | A1 | 10/2017 | Misle et al. |
| 2018/0014926 | A1 | 1/2018 | Cassani |
| 2018/0185022 | A1 | 7/2018 | Mohamed et al. |
| 2018/0193015 | A1 | 7/2018 | Denham et al. |
| 2018/0221133 | A1 | 8/2018 | Lund |
| 2018/0271640 | A1 | 9/2018 | Woodruff et al. |

FOREIGN PATENT DOCUMENTS

| | | |
|---|---|---|
| CN | 204600572 U | 9/2015 |
| CN | 107582182 A | 1/2018 |
| DE | 69820014 T2 | 9/2004 |
| DE | 102008044855 A1 | 3/2010 |
| DE | 20217001689 U1 | 6/2017 |
| EP | 0415915 B1 | 10/1996 |
| EP | 2359754 A2 | 8/2011 |
| ES | 1060450 | 9/2005 |
| JP | 2007-283061 | 11/2007 |
| KR | 10-1611732 | 4/2016 |
| WO | WO 2010/103467 A1 | 9/2010 |
| WO | WO 2015/072797 A1 | 5/2015 |
| WO | WO 2018//009637 A1 | 1/2018 |

\* cited by examiner

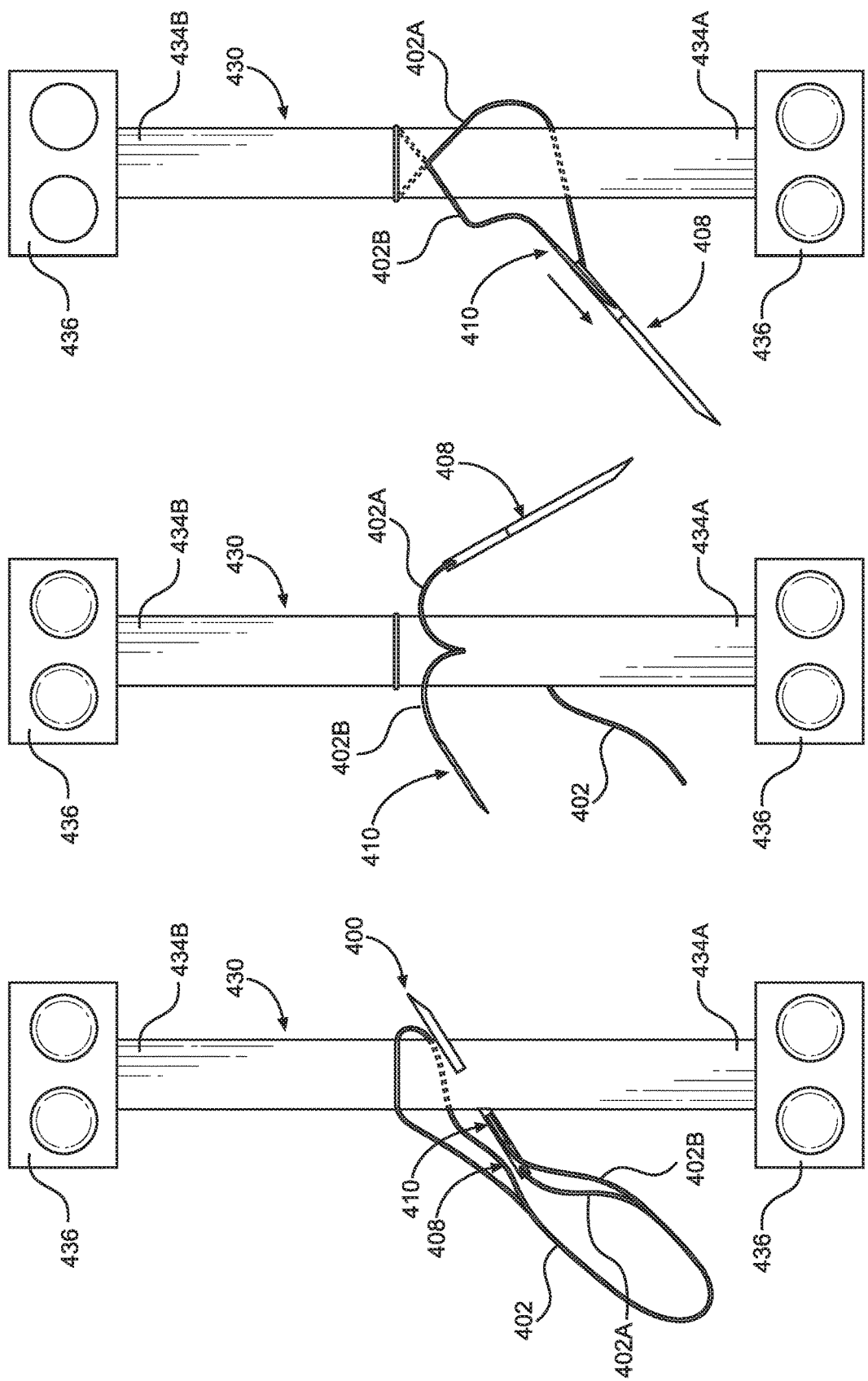

METHOD AND APPARATUS FOR DOUBLE LOOP STITCHING

CROSS-REFERENCE TO RELATED APPLICATIONS

This application claims the benefit of U.S. Provisional Patent Application No. 62/586,690, filed on Nov. 15, 2017 and entitled METHODS AND SYSTEMS FOR DOUBLE LOOP STITCHING, which is incorporated herein by reference in its entirety.

FIELD OF THE INVENTION

This invention generally relates to a method and apparatus for surgical stitching. More specifically, the present invention, relates to an improved method and apparatus for carrying out ligament reconstruction surgery using a whip stitched soft tissue graft.

BACKGROUND OF THE INVENTION

Ligament replacement or repair is very common amongst athletes and active individuals. Two examples of ligaments that are commonly injured and require replacement or repair are the anterior cruciate ligament (ACL) and the posterior cruciate ligament (PCL). The ACL and the PCL are bands of fibrous tissue that are located at the knee joint and that connect the tibia to the femur. These ligaments assist in controlling the flexion and extension of the leg, and sprains and tears, particularly to the ACL, are among the most common sports-related injuries. Injuries to the ACL often occur when the athlete turns or moves suddenly when running or jumping. Depending on the nature and severity of the injury, treating a torn or strained ACL or PCL may or may not require surgery. Non-surgical methods include bracing and physical therapy. On the other hand, when the damage is more severe, a torn ACL or PCL may be stitched back together using sutures. In even more severe cases, where the ligament cannot be stitched, it is typically replaced entirely.

With initial reference to FIGS. 1 and 2, a knee 100 is depicted after undergoing an ACL replacement procedure. In a typical ACL replacement surgery, the torn ligament is replaced by a soft tissue graft 102, which may be taken from the patient's own body or from a donor. The graft is commonly taken from the knee, hamstring, or quadriceps. The surgeon then uses a needle and heavy-duty, non-degradable suture to reinforce the ends of the graft. The graft is then implanted into the knee and affixed so that it serves the same anatomical function that the torn ACL served prior to tearing. More particularly, the graft provides a support structure that enables a new ligament to grow. During the procedure, the first step is to remove the torn ligament. Next, the graft is prepared for insertion into the knee. Among other things, this preparation may include folding the replacement tendon onto itself to form layered strands of tissue (FIG. 2) and then stitching the strands together to create a graft 102 with one or more stitched sections 104 that have adequate strength and the correct length. Once the graft 102 has been prepared, holes or "tunnels" 106 are drilled into the tibia 108 and the femur 110. Ends 112 of the graft 102 are then inserted into the tunnels 106 and are fixed in place. The above-described process for graft preparation is known in the art and is discussed, for example, in U.S. Pat. No. 8,298,284, entitled "Whip Stitched Graft Construct and Method of Making the Same" (hereinafter, "Arthrex").

A conventional graft preparation process, such as that described in Arthrex, is illustrated in FIGS. 3A-3E. According to the illustrated method, one end (such as distal end 114) of a graft 116 is securely held by a stationary work station 118. A continuous or closed loop of suture material 120 having a needle 122 is placed around the graft 116 such that the graft passes through the loop. A proximal end 124 of the graft 116 is held by hand or by a tool in a user's hand. Proximal end 124 of the graft 116 is not connected to the work station 118; rather, the proximal end is typically grasped by hemostats, forceps, etc. Next, the needle 122 is inserted through a first side of the graft 116 (e.g., bottom of the graft) and the needle and suture 120 are pulled through to the second side of the graft (e.g., the top of the graft). From there, the process of inserting the needle 122 through the first side of the graft 116 and then pulling the needle and suture 120 through to the second side of the graft is repeated multiple times until the desired number of stitches have been created. Ideally, the needle 122 enters the same side of the graft 116 for each stitch. To move the needle 122 back to the bottom of the graft in preparation for each subsequent stitch, the proximal end 124 of the graft 116 is passed through the loop of the suture material 120. Put differently, the loop of the suture material 116 passes around the proximal end 124 of the graft 116. This step typically requires the user to release their grip on the proximal end 124 of the graft 116 so that the proximal end can pass through the loop. Passing the loop of the suture material 116 around the proximal end 124 of the graft 116 requires spreading the loop to form a first loop portion 126 and a second loop portion 128. When the needle 122 is brought back below the graft 116, the first loop portion 126 passes over the left-most edge of the graft 116 and the second loop portion 128 of the suture material passes over the right-most edge of the graft. Those loop portions 126, 128 come back together below the graft 116. From there, the needle 122 and suture material 120 are inserted through the graft 116 repeatedly to create a pattern of stitches, often called a "whipstitch" pattern, that extends along at least a portion of the graft 116.

One problem with the conventional graft preparation process discussed above is that only the distal end 114 of the graft 116 is fixed and stationary when creating the whipstitch pattern. This enables the non-fixed proximal end 124 of the graft 116 to move during the stitching process. Movement of the graft 116 during the stitching process can result in non-uniform stitch positioning and spacing, which can ultimately lead to failure of the graft, such that a revision (i.e., follow-up) surgical procedure is required.

What is needed, therefore, is a method and apparatus for creating a double-loop stitch in a ligament graft while both ends of the graft remain stationary and fixed.

Notes on Construction

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

Terms concerning attachments, coupling and the like, such as "attached", "connected" and "interconnected", refer to a relationship wherein structures are secured or attached to one another either directly or indirectly through intervening structures, as well as both moveable and rigid attachments or relationships, unless specified herein or clearly indicated by context. The term "operatively connected" is such an attachment, coupling or connection that allows the pertinent structures to operate as intended by virtue of that relationship.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

The apparatus and method disclosed herein may be used for traditional sewing processes, such as joining fabric or textiles in the production of clothing, etc., in surgical procedures, and other similar processes. The term "thread" is used broadly to refer to textile-type strands used in traditional sewing processes, to refer to medical sutures for use in performing surgery, and the like. Similarly, the term "sewing" is used broadly to refer to the traditional sewing type processes or surgical procedures that use needle and thread. Lastly, the term "sewing material" is used broadly to refer to textile or other types of materials used in traditional sewing type processes or to materials used in surgical procedures, such as ligaments.

SUMMARY OF THE INVENTION

The above and other needs are met by a sewing needle for passing a thread through a sewing material. The needle includes a needle tip configured to initially pass through said sewing material and a trailing end located at an opposite end of the needle from the needle tip. Preferably, the needle tip is integrally formed at an end of the first needle portion. A first needle portion follows the needle tip through said sewing material and a second needle portion is removably connected to the first needle portion and follows the needle tip through said sewing material. The needle also includes a first thread connection located on the first needle portion that is configured to carry a first portion of said thread through the sewing material and a second thread connection located on the second needle portion that is configured to carry a second portion of said thread through the sewing material.

In some embodiments, the needle includes a receiver having an opening that is formed on the first needle portion. An end is formed on the second needle portion that is sized and configured for sliding insertion into the receiver of the first needle portion via the opening in order to removably connect the second needle portion to the first needle portion. In some embodiments, the receiver is an elongate hollow receiver having a closed end that is located proximate the needle tip and opposite the opening. The end of the of the second needle portion may be provided with a narrowed tip that is configured to initially engage the opening of the receiver for assisting in inserting the second needle portion into the receiver. In certain cases, the end of the second needle portion is a second needle tip. The needle may be a straight needle or a curved needle. Additionally, in some embodiments, at least one of the first and second thread connections is swaged (i.e., eyeless). Additionally or alternatively, at least one of the first and second thread connections is eyed. To prepare the needle for use, a thread may be connected to the needle. More particularly, a first end of the thread may be connected to the first needle portion via the first thread connection and a second end of the thread may be connected to the second needle portion via the second thread connection. The thread may be connected to the needle by non-removable swaged connections. Lastly, the needle and thread may be used in surgical applications using surgical grade materials suitable for use in a human (or other) body or non-surgical applications, such as in the production or manipulation of textiles.

Also disclosed herein is a method for providing a double loop stitch in a sewing material, such as a graft used in ACL reconstruction surgery, using the presently disclosed two-part needle. Portions of the graft are fixedly mounted to connecting locations of a stationary support such that a portion of the sewing material extends between the connecting locations of the stationary support. A first stitch is formed in the portion between the connecting locations by passing the needle through the sewing material in a first direction such that the needle enters a first face and exits a second face and such that the first and second ends of the thread are also passed through the sewing material. After the needle passes through the sewing material, the first needle portion is disconnected from the second needle portion and the first and second ends of the thread are separated. The first needle portion and the first end of the thread are moved back to the first face of the sewing material by being passed outside a first side edge of the sewing material. Similarly, the second needle portion and the second end of the thread are moved back to the first face of the sewing material by being passed outside the second side edge of the sewing material. Next, the first needle portion is reconnected to the second needle portion in preparation for forming a second stitch. The above process is repeated to form the required number of stitches along the length of the graft. After all required stitches are formed, the sewing material may be removed from the stationary support.

In certain embodiments, a loop of thread may be formed around the sewing material prior to forming the first stitch. In that case, the portion of the sewing material extending between the spaced apart connecting locations is located within a loop formed by the thread between the first and second ends thereof when the first needle portion is connected to the second needle portion. In certain embodiments, the second end of the thread passes through the sewing material before the first end of the thread passes through the sewing material. In other embodiments, the second end of the thread passes through the sewing material substantially simultaneously with the first end of the thread passing through the sewing material. According to certain embodiments, subsequent stitches are spaced longitudinally away from the first stitch along the length of the sewing material. In some embodiments, where the second needle portion comprises a second needle tip, the two needle tips may be passed through the sewing material separately from one another in different locations in order to create custom stitch patterns.

BRIEF DESCRIPTION OF THE DRAWINGS

The presently preferred embodiments of the invention are illustrated in the accompanying drawings, in which like reference numerals represent like parts throughout, and in which:

FIGS. 11A-11E illustrate a process for providing a double loop stitch in a material that is fixed at both ends using a two-part needle according to a method of the present invention.

DESCRIPTION OF THE PREFERRED EMBODIMENTS OF THE INVENTION

Figure 1:
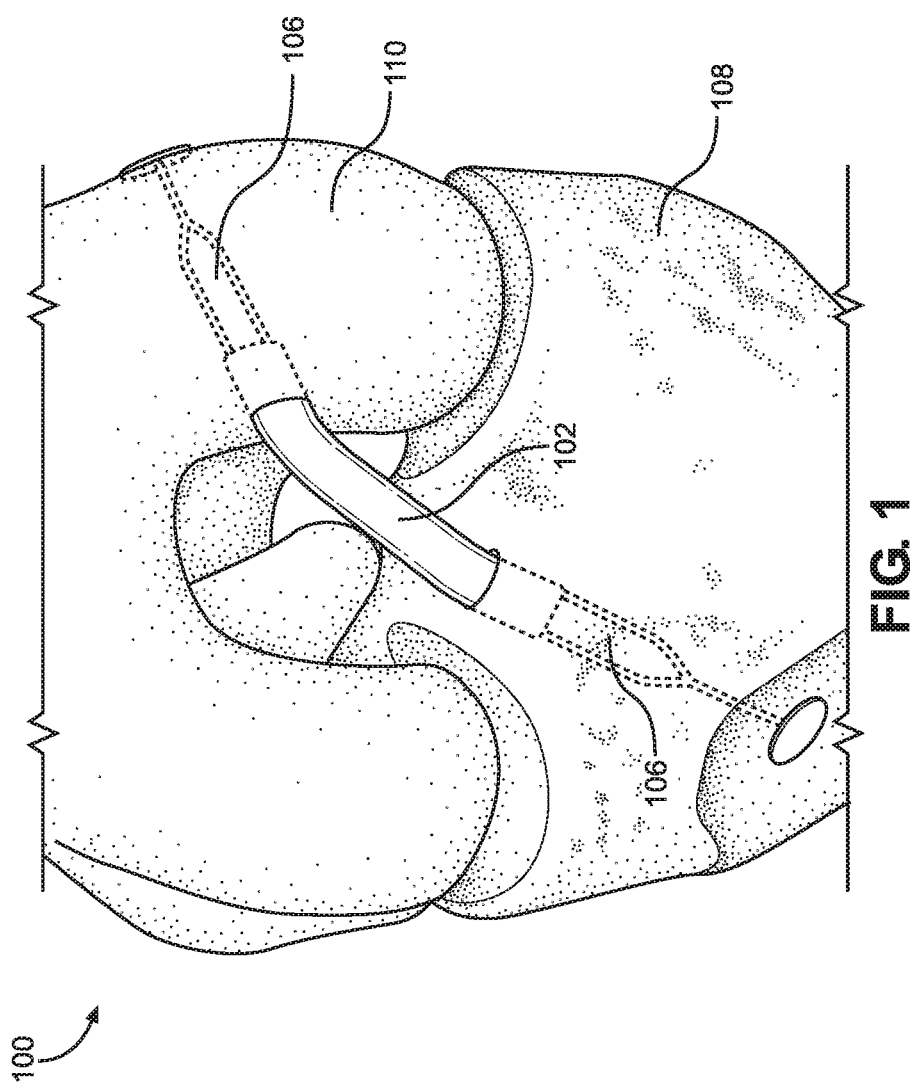
FIG. 1 depicts a knee following an ACL reconstruction procedure.
Figure 2:
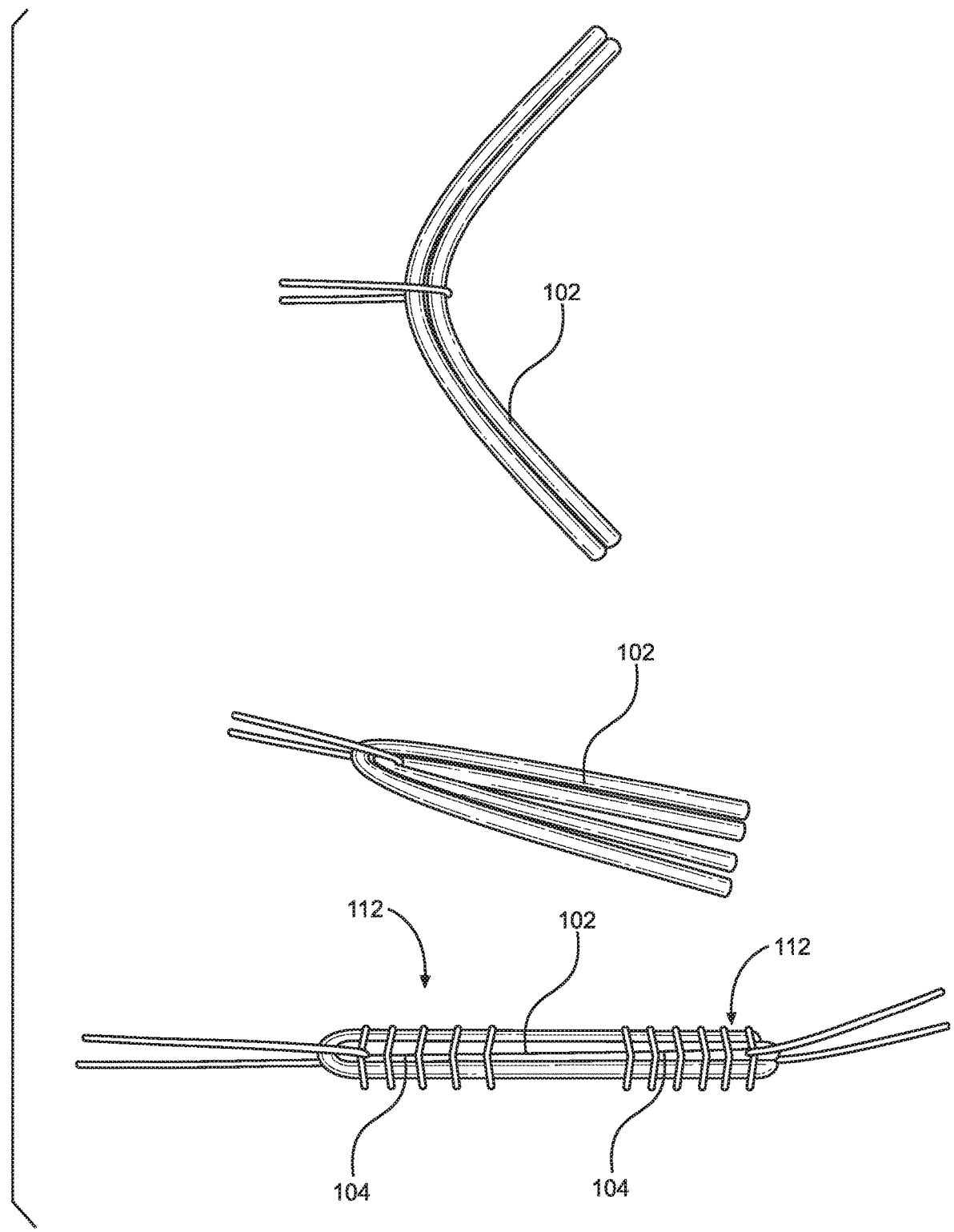
FIG. 2 provides side elevation views depicting a tendon being folded and sutured in preparation for an ACL reconstruction procedure.

This description of the preferred embodiments of the invention is intended to be read in connection with the accompanying drawings, which are to be considered part of the entire written description of this invention. The drawings are not necessarily to scale, and certain features of the invention may be shown exaggerated in scale or in somewhat schematic form in the interest of clarity and conciseness.

With reference now to FIGS. 4-9, there is provided a two-part sewing needle 400 for passing a thread 402 through a sewing material. The sewing needle 400 includes a needle tip 404 configured to initially pass through said sewing material. A trailing end 406 is located at an opposite end of the needle 400 from the needle tip 404 and is generally the last portion of the needle 400 to pass through the sewing material. The needle 400 in this case is substantially linear along its length (i.e., along a line extending between the needle tip 404 and the trailing end 406). However, in other cases, at least a portion of the needle is curved along its length. The needle 400 includes a first needle portion 408 that is configured to follow the needle tip 404 through the sewing material. In preferred embodiments, the needle tip 404 is integrally formed at an end of the first needle portion 408. Additionally, the needle 400 includes a second needle portion 410 that is configured to removably connect to the first needle portion 408 and to also follow the needle tip 404 through the sewing material. Depending on the respective dimensions (e.g., length) of the first and second needle portion 408, 410, the trailing end 406 of the needle 400 may be located on either the first needle portion or the second needle portion.

The continuous thread 402 is connected to both the first and second needle portions 408, 410. A first thread connection 412 is located on the first needle portion 408 and is configured to carry a first portion 402A of said thread 402 through the sewing material. Likewise, a second thread connection 414 is located on the second needle portion 410 and is configured to carry a second portion 402B of said thread 402 through the sewing material. In the embodiment shown, a single strand of thread 402 extends between the first and second needle portions 408, 410, with one end of the thread strand being fixed at the first thread connection 412 and the other end of the thread strand being fixed at the second thread connection 414. However, the thread 402 may form a continuous loop passing through both thread connections 412, 414, such that at least two strands of thread extend between the first and second needle portions 408, 410. An advantage of the continuous loop is that the needle portions 408, 410 may "float" along the thread 402 and may be re-centered on the thread during the sewing process. Additionally, the thread connections 412, 414 illustrated are openings (or eyes) that the thread 402 is passed through. In other embodiments, the thread connections 412, 414 are swaged (or eyeless) connections, where the thread 402 is integrally formed with an end of the needle portions 408, 410.

The needle 400 and thread 402 may be used for traditional sewing tasks, such as in the manufacture or manipulation of textiles. In other embodiments, the needle 400 and thread 402 are used for surgical procedures and are made from surgical grade materials. When used for surgical procedures, an advantage of the swaged end design is reduced trauma to the patient.

The first needle portion 408 and the second needle portion 410 are configured to selectively and removably connect together, such that they pass substantially simultaneously through the sewing material. A receiver 416 is located on the first needle portion 408 and is sized and configured to receive the second needle portion 410 for removably connecting the first and second needle portions together. In this particular embodiment, the receiver 416 is an elongate fully-enclosed canal that has been machined (e.g., bored) into and extends along at least a portion of the length of the first needle portion 408. The receiver 416 has an opening 424 at one end and a stop 420 located at the opposite end. In this particular case, the stop 420 is created by boring the elongate receiver 416 only partially through the first needle portion 408.

An end 422 formed on the second needle portion 410 is sized for sliding insertion into the receiver 416 via the opening 424. As the second needle portion 410 slides into the receiver 416, the end 422 contacts the stop 420 and the stop prevents the second needle portion from passing entirely through the first needle portion 408. Advantageously, contacting the end 422 with the stop 420 provides tactile feedback to the user that provides assurance that the second needle portion 410 has been fully inserted into and correctly located within the first needle portion 408. Preferably, the end 422 of the of the second needle portion 410 is provided with a narrowed tip configured to initially engage the opening 424 of the receiver 416 for assisting in inserting and guiding the second needle portion into the receiver. For example, in certain embodiments, the end 422 of the second needle portion 410 comprises a second needle tip. However, in other embodiments, the end 422 is blunted (i.e., not sharp) in order to help prevent inadvertent injury.

In certain embodiments, a partially enclosed (i.e. concaved) post section 426 that extends beyond the opening 424 is formed on the first needle portion 408. One purpose of the post section 426 is to support and protect the portion of the second needle portion 410 that extends beyond the opening 424. The concaved sides of the post section 426 extend partially around the second needle portion 410 and help protect the second needle portion from damage (e.g., bending) while still allowing the second needle portion to be easily accessed. The post section 426 also provides a location for the first thread connection 412, which is formed near the end of post section. Preferably, the post section 426 is sized such that the first thread connection 412 is fully exposed when the second needle portion 410 is fully inserted into the receiver 416 of the first needle portion 408. Likewise, the second thread connection 414 is also preferably fully exposed when the second needle portion 410 is fully inserted into the receiver 416 of the first needle portion 408.

Figure 10:
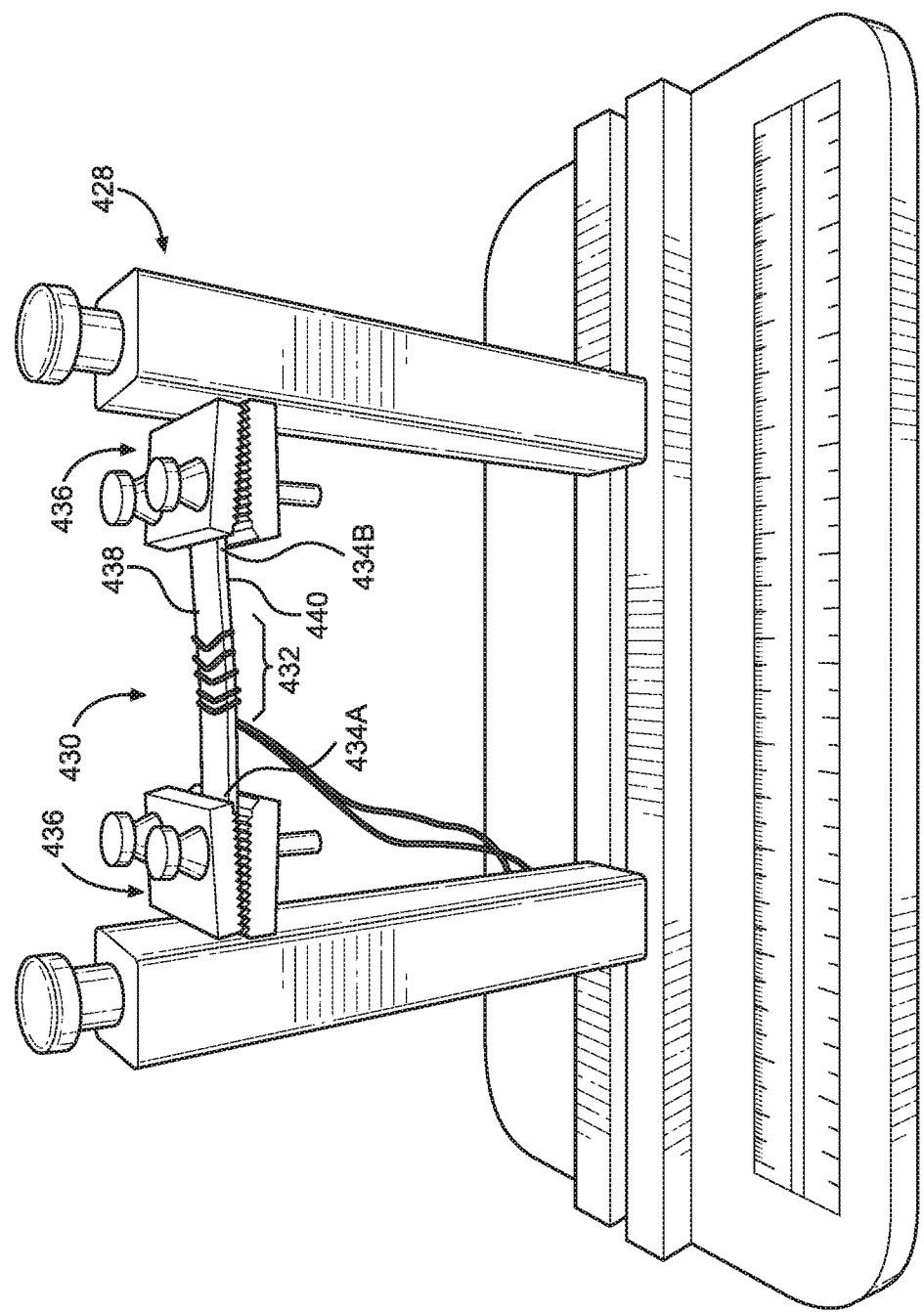
FIG. 10 depicts a graft preparation station including a graft fixed at both ends and having a portion provided with double loop stitches according to a method of the present invention.

The above-described two-part needle 400 may be used in carrying out an improved method for creating a whipstitch, including particularly in preparing a graft in a medical procedure, such as an ACL reconstruction surgery. With reference now to FIG. 10, a graft preparation station 428 with an exemplary ACL graft 430 having a whip stitched section 432 is shown. Each end 434A, 434B of the graft 430 is securely held by graft clamps 436 of the graft preparation station 428 such that a portion of the graft extends between the clamps and the graft is held stationary and under slight tension. Positioning the graft 430 between the clamps 436 makes the top face 438 and bottom face 440 of the graft, where the needle 400 must pass during the sewing procedure, easily accessible.

Figure 11E:
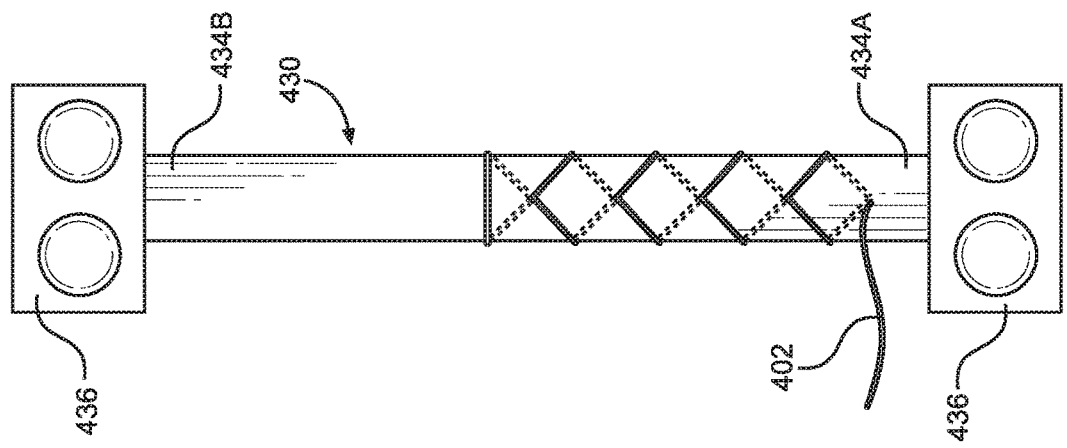

In FIGS. 11A-11E, a process of whip stitching a tendon 430 (enlarged for clarity) using a needle 400 is illustrated. Referring initially to FIG. 11A, to begin the stitching process, the graft 430 is placed into a graft station, as discussed above, such that both ends 434A, 434B of the graft are securely held by graft clamps 436. A thread 402 is connected to a needle 400 such that a first portion 402A of the thread is connected to the first needle portion 408 and a second portion 402B of the thread is connected to the second needle portion 410. The needle 400, arranged in a connected configuration such that the first and second needle portions 408, 410 are connected together, is then inserted through the graft 430 in a first direction such that the needle enters a first portion (e.g., bottom face 440) of the graft and exits a second portion (e.g., top face 438). By pulling the needle 400 through the graft 430, both needle portions 408, 410 and both thread portions 402A, 402B are also carried through the graft.

Figure 11D:
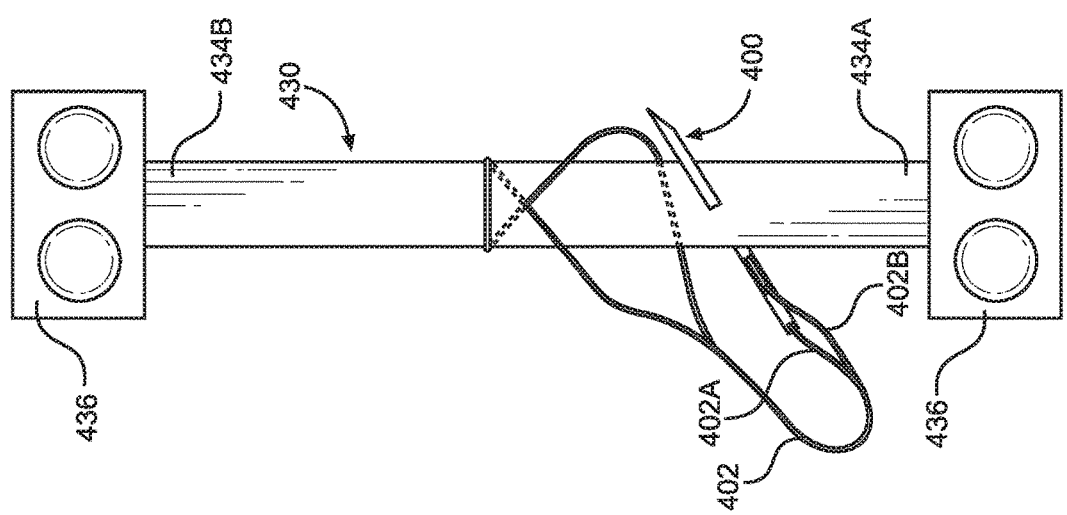

With reference to FIG. 11B, once the needle 400 has been pulled through the graft 430, forming the first stitch, the first needle portion 408 is separated from the second needle portion 410, which also separates the thread portions 402A, 402B. Once separated, the thread portions 402A, 402B are brought around the outside of the graft 430 back adjacent to the first portion (e.g., bottom face 440) in preparation for forming a second stitch. In the illustrated process, the first thread portion 402A passes around the right edge of the graft 430 and the second thread portion 402B passes around the left of the graft. As shown in FIG. 11C, once the thread portions 402A, 402B are moved back adjacent to the first portion (e.g., bottom face 440) of the graft 430, the first and second needle portions 408, 410 are reconnected. As shown in FIGS. 11D and 11E, once the first and second needle portions 408, 410 are reconnected, the needle 400 is ready to form a second and subsequent stitches along the length of the graft by repeating the above-described process. After the required number of stitches are provided, the graft 430 is removed from the clamps 436. In the illustrated process, stitches are provided in only one end 434A of the graft 430. However, using the same process, stitches may be provided at either or both ends 434A, 434B of the graft 430.

Figure 3C:
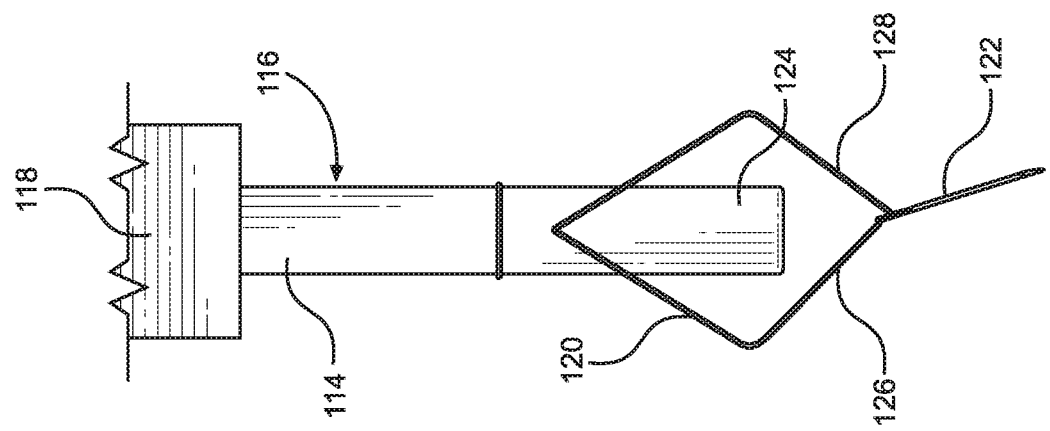
FIGS. 3A-3E illustrate a conventional method for providing a double loop stitch where the material being sewn is fixed only at one end.
Figure 3B:
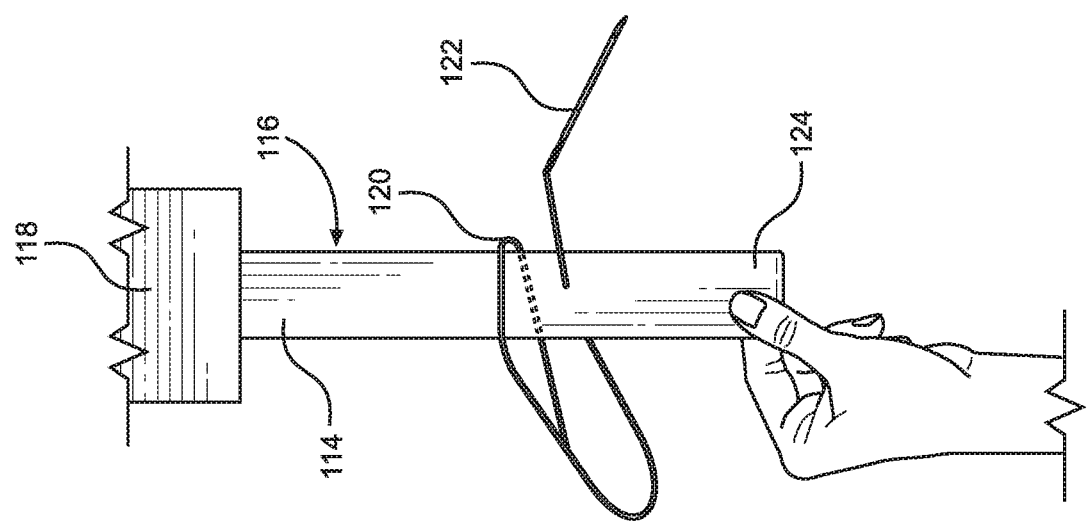
Figure 3A:
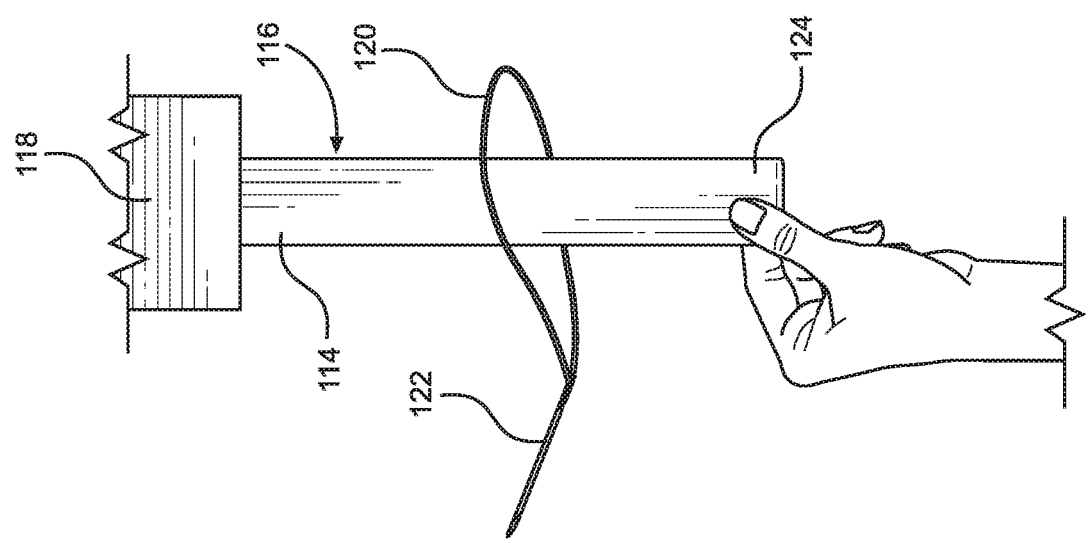
Figure 3E:
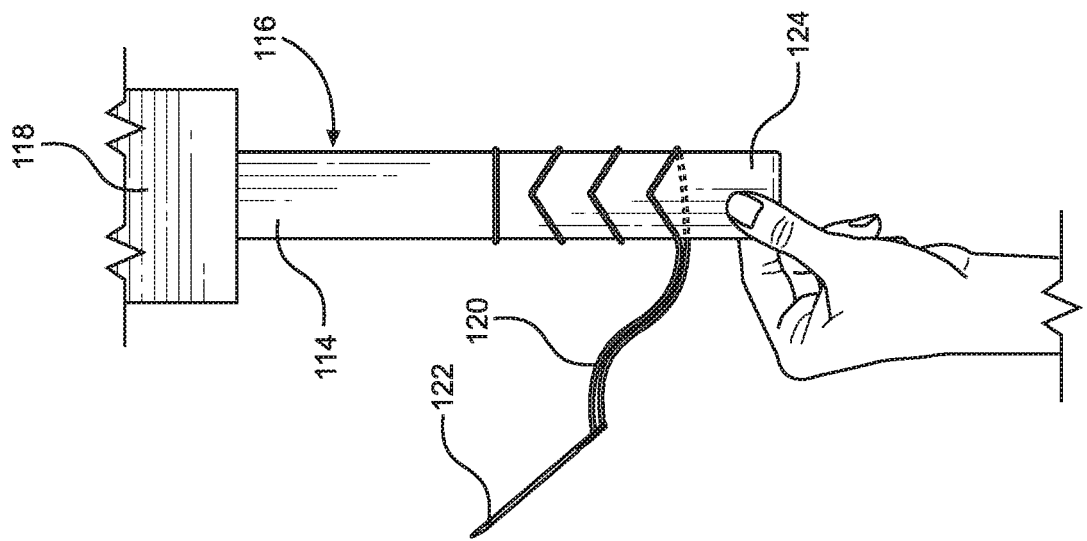
Figure 3D:
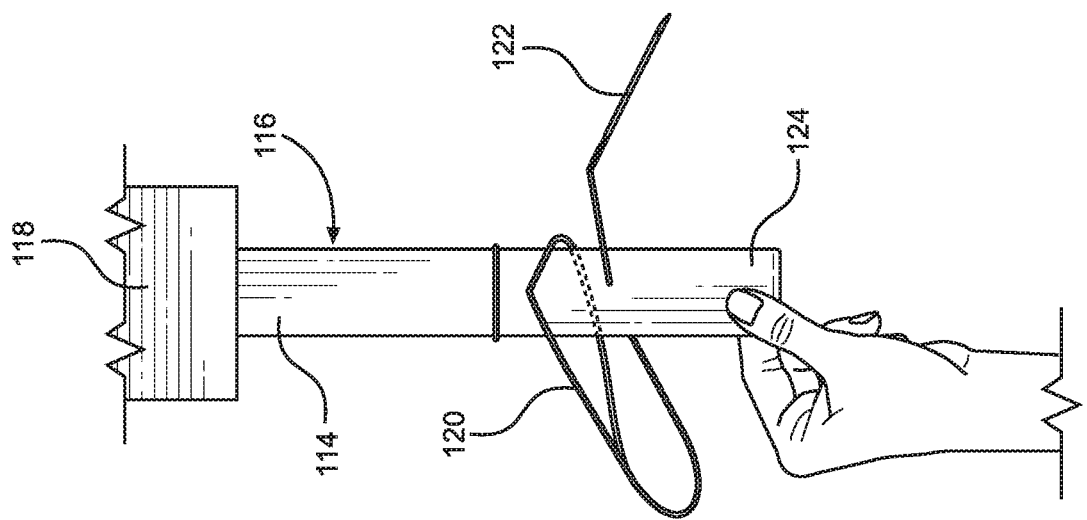
Figure 4:
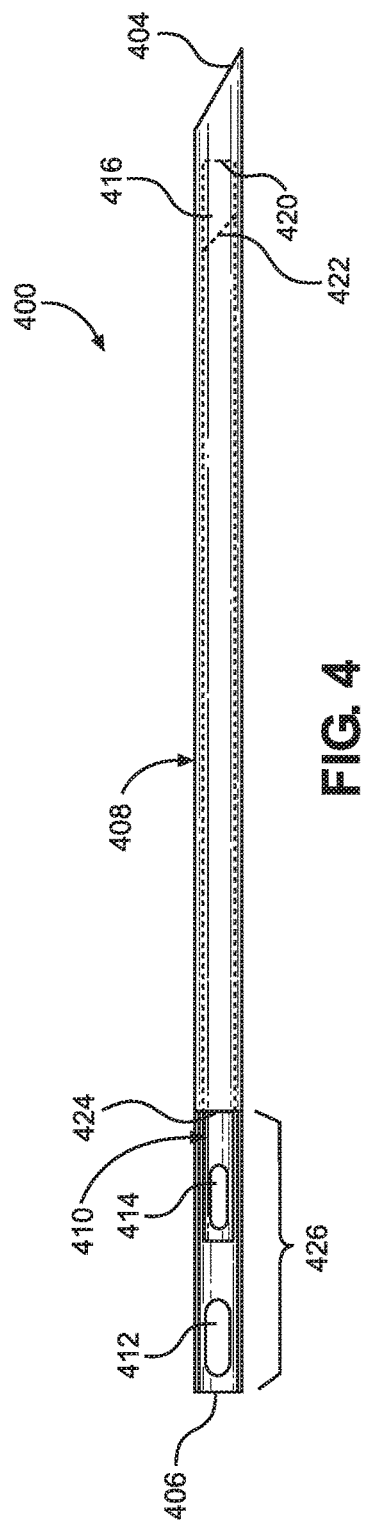
FIG. 4 is a sectional view depicting a needle formed by a first needle portion and a second needle portion inserted into an elongate hollow receiver of the first needle portion according to an embodiment of the present invention.
Figure 5:
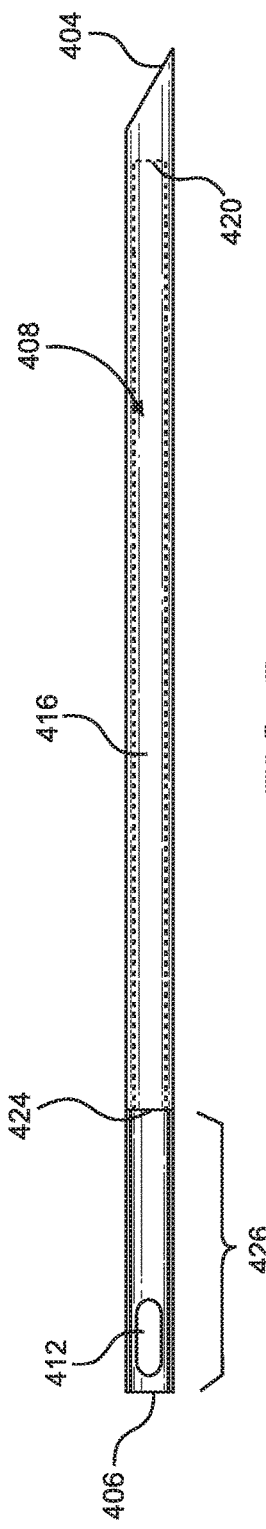
FIG. 5 is a sectional view depicting the first needle portion of FIG. 4.
Figure 6:
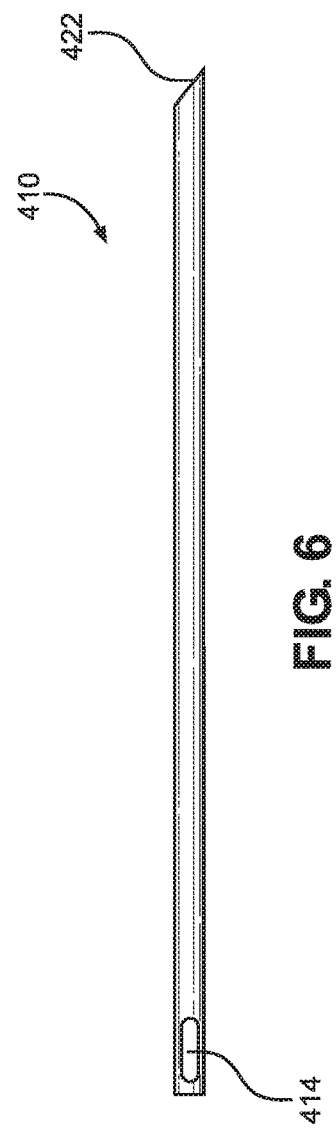
FIG. 6 is a sectional view depicting the second needle portion of FIG. 4.
Figure 7:
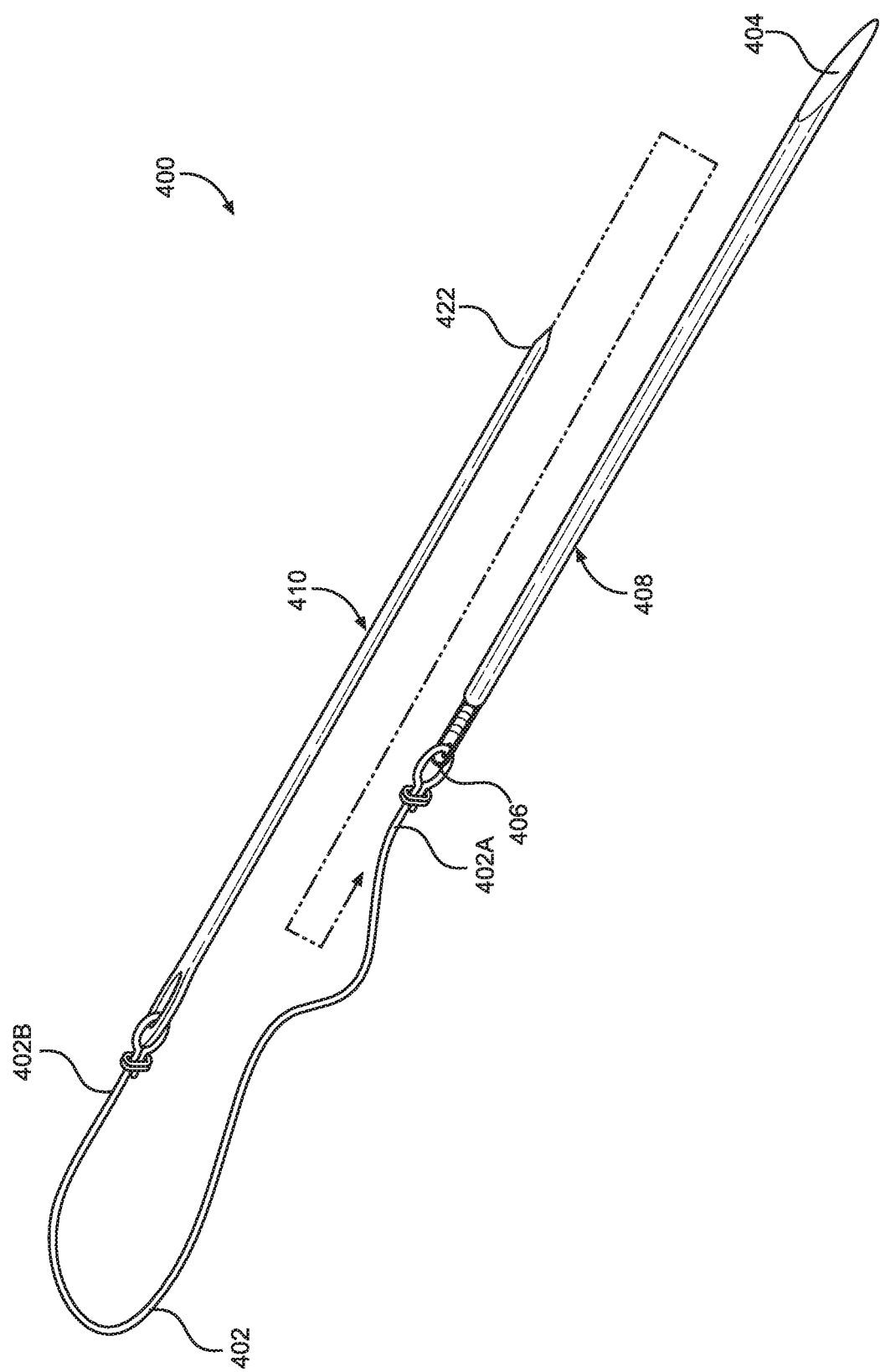
FIGS. 7 and 8 are perspective views depicting a thread connecting a first needle portion and second needle portion of a two-part needle in a disconnected configuration.
Figure 8:
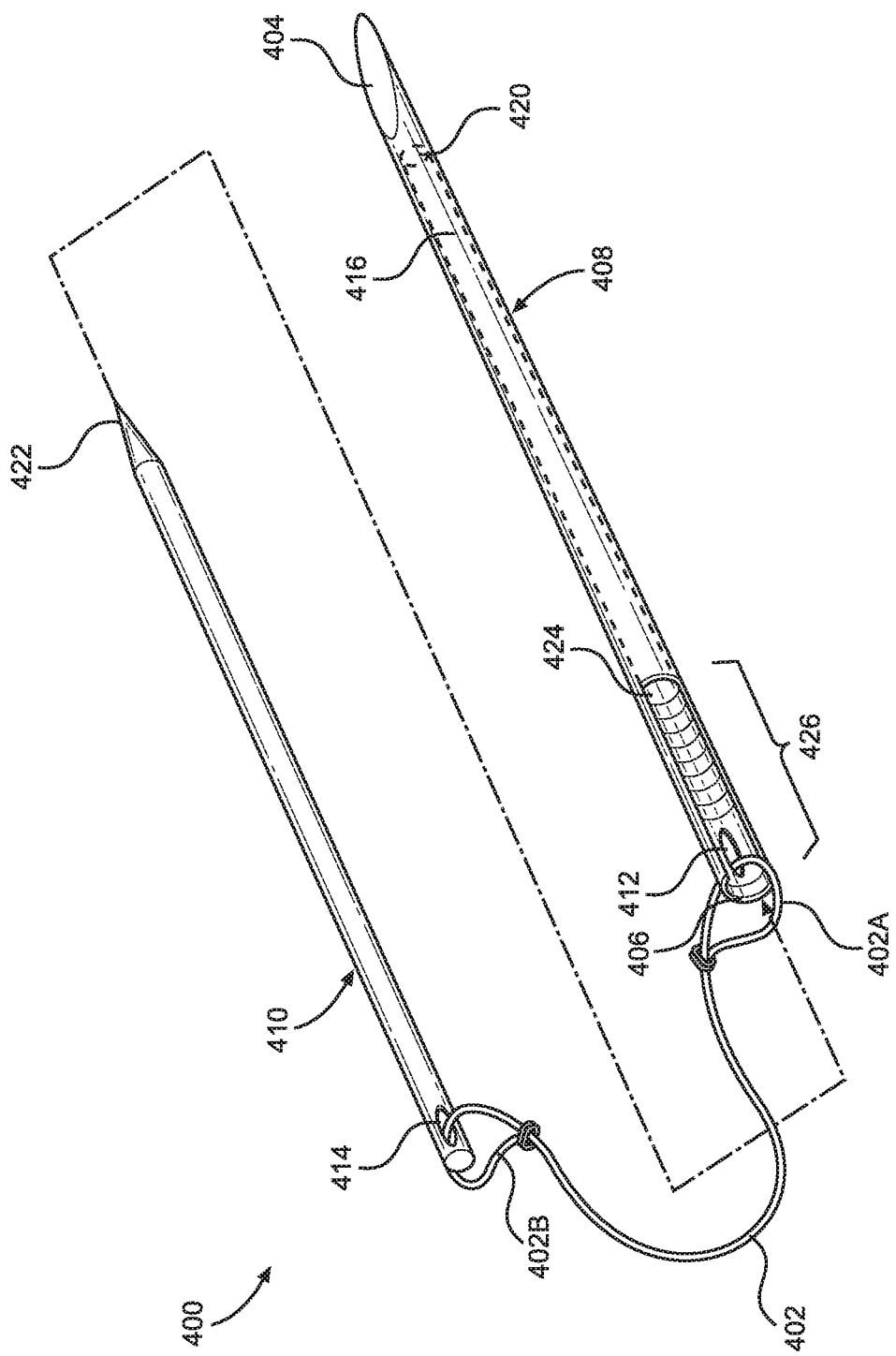
Figure 9:
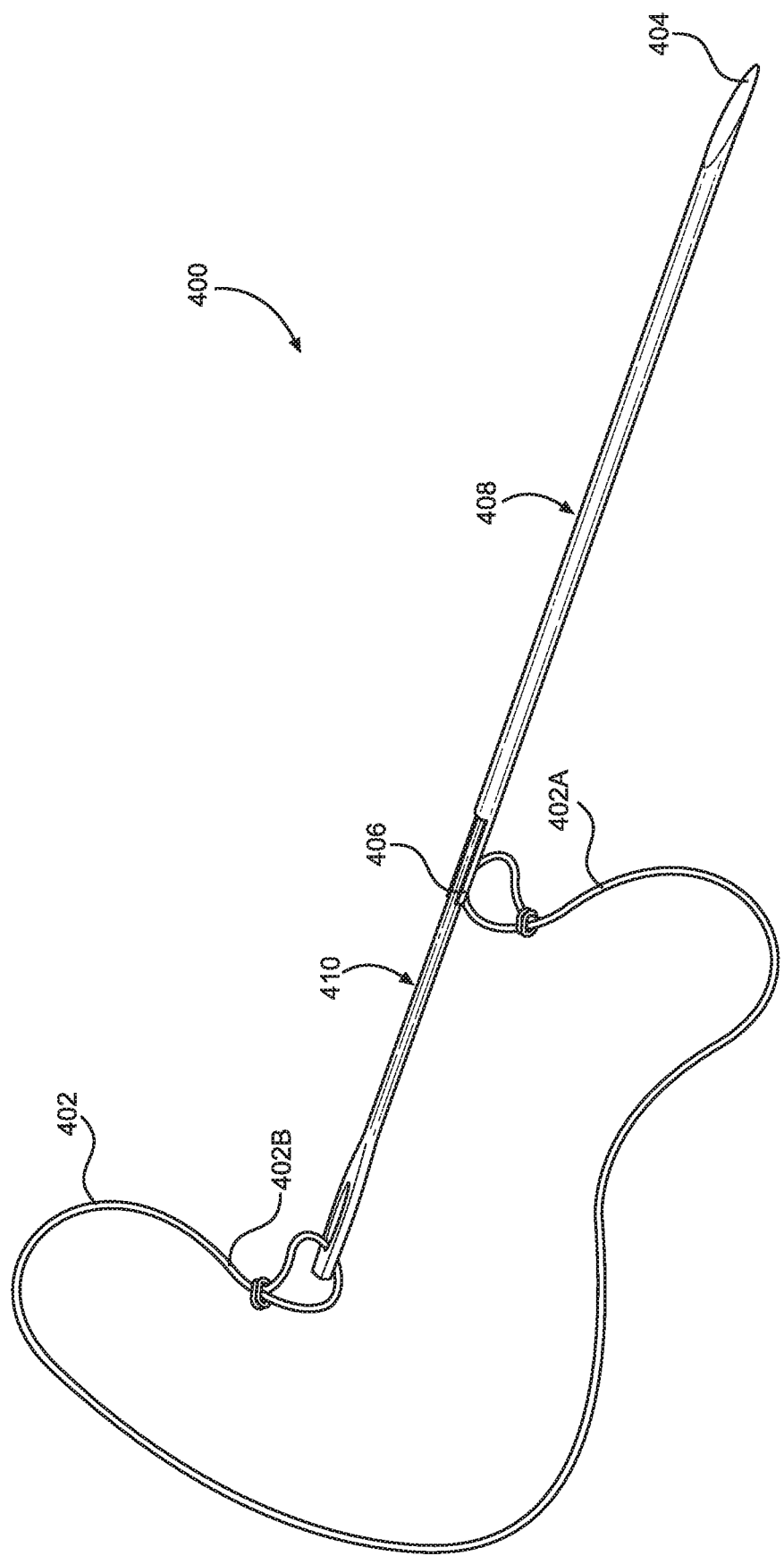
FIG. 9 depicts the second needle portion of FIGS. 7 and 8 partially inserted into the first needle portion.

As previously discussed, in conventional whipstitch methods, after forming a stitch the needle and thread are brought back to the first face of the graft by passing over a free end of the graft that is not fixed in a graft preparation station (see, e.g., Figure FIG. 3C). As such, that end of the graft freely moves during the preparation process, which may damage the graft and could result in inconsistent stitching. That inconsistency may impact the strength and quality of the graft and, ultimately, the failure rate of the surgery. In contrast, using the above-described two-part needle and stitching method, both ends of the graft remain fixed throughout the entire graft preparation process. This allows the stitching process to be carried out more easily and also more consistently than conventional methods.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

What is claimed is:

1. A sewing needle for passing a thread through a sewing material to form a stitch from the thread extending through the sewing material, the sewing needle comprising:
   a first needle portion having a needle tip;
   a second needle portion configured to removably connect to the first needle portion and, when removably connected to the first needle portion, to follow the needle tip and to pass through the sewing material substantially simultaneously with the first needle portion;
   a first thread connection disposed on the first needle portion configured to fixedly connect to a first portion of the thread and to carry the first portion of said thread through the sewing material; and
   a second thread connection disposed on the second needle portion configured to fixedly connect to a second portion of the thread and to carry the second portion of said thread through the sewing material,
   wherein, when the second needle portion is removably connected to the first needle portion, the first and second thread connections are configured to carry the first and second portions of the thread through the sewing material substantially simultaneously by the first needle portion and the second needle portion, respectively, such that a third portion of the thread that is located between the first and second portions of the thread trails behind the first and second needle portions to remain extended through the sewing material.

2. The needle of claim 1 wherein the needle tip is integrally formed at an end of the first needle portion.

3. The needle of claim 1 further comprising:
   a receiver having an opening formed on the first needle portion; and
   an end formed on the second needle portion that is sized and configured for sliding insertion into the receiver of the first needle portion via the opening in order to removably connect the second needle portion to the first needle portion.

4. The needle of claim 3 comprising an elongate hollow receiver having a closed end located proximate the needle tip and opposite the opening.

5. The needle of claim 3 wherein the end of the of the second needle portion is provided with a narrowed tip configured to initially engage the opening of the receiver for assisting in inserting the second needle portion into the receiver.

6. The needle of claim 3 wherein the end of the second needle portion comprises a second needle tip.

7. The needle of claim 1 wherein the needle is substantially linear along its length.

8. The needle of claim 1 wherein at least a portion of the needle is curved along its length.

9. The needle of claim 1 wherein at least one of the first and second thread connections is swaged.

10. The needle of claim 1 wherein at least one of the first and second thread connections is eyed.

11. The needle of claim 1 further comprising a thread having a first end connected to the first needle portion via the first thread connection and a second end connected to the second needle portion via the second thread connection.

12. The needle of claim 11 wherein the thread is connected to the first thread connection and second thread connection by non-removable swaged connections.

13. The needle of claim 1 wherein the needle is formed using surgical grade materials suitable for use in a human body.

14. A method for providing a double loop stitch comprising:
A. providing a needle having: a first needle portion, a second needle portion that is removably connected to the first needle portion, a first thread connection disposed on the first needle portion, a second thread connection disposed on the second needle portion;
B. providing a thread having a first end connected to the first needle portion via the first thread connection and a second end connected to the second needle portion via the second thread connection;
C. providing a sewing material having a proximal portion, a distal portion, a first face, a second face opposing the first face, a first side edge, and a second side edge opposite the first side edge;
D. providing a stationary support having spaced apart connecting locations;
E. connecting the proximal portion and the distal portion of the sewing material to the spaced apart connecting locations of the stationary support such that a portion of the sewing material between the proximal and distal portions of the sewing material extends between the spaced apart connecting locations of the stationary support;
F. forming a first stitch by passing the needle through the sewing material in a first direction such that the needle enters the first face and exits the second face and such that the first and second ends of the thread are also passed through the sewing material;
G. disconnecting the first needle portion from the second needle portion and separating the first and second ends of the thread;
H. passing the first needle portion and the first end of the thread outside the first side edge of the sewing material in a second direction;
I. passing the second needle portion and the second end of the thread outside the second side edge of the sewing material in a second direction;
J. connecting the first needle portion to the second needle portion;
K. forming a subsequent stitch by passing the needle through the sewing material in a first direction such that the needle enters the first face and exits the second face and such that first and second ends of the thread are also passed through the sewing material; and
L. removing the proximal portion and the distal portion of the sewing material from the spaced apart connecting locations of the stationary support.

15. The method of claim 14 further comprising the steps of:
M. prior to Step (F), locating the portion of the sewing material extending between the spaced apart connecting locations within a loop formed by the thread between the first and second ends thereof when the first needle portion is connected to the second needle portion; and
N. after Step (F), pulling the thread through the sewing material such that a portion of the loop contacts the second face of the sewing material.

16. The method of claim 14 wherein the second end of the thread passes through the sewing material before the first end of the thread passes through the sewing material.

17. The method of claim 14 wherein the second end of the thread passes through the sewing material substantially simultaneously with the first end of the thread passing through the sewing material.

18. The method of claim 14 wherein the subsequent stitch is spaced longitudinally away from the first stitch along the length of the sewing material.

* * * * *